United States Patent [19]

Perrin et al.

[11] 4,154,968

[45] May 15, 1979

[54] BACTERICIDIC AND FUNGICIDIC CHLOROMETHYLISOPROPYPHENOLS

[75] Inventors: Robert M. Perrin, Saint-Didier-au-Mont D'Or; Giséle Aureille, Champigny sur Marne; Marie-Françoise Vincent-Falquet, Caluire; Edmond Collange, Saint-Martin-de-Valamas, all of France

[73] Assignee: Chrysa, Rhone, France

[21] Appl. No.: 878,884

[22] Filed: Feb. 17, 1978

Related U.S. Application Data

[62] Division of Ser. No. 357,812, May 7, 1973, Pat. No. 4,098,828.

[51] Int. Cl.$^2$ .............................................. C07C 39/27
[52] U.S. Cl. ................................................... 568/774
[58] Field of Search .............................. 568/774, 781

[56] References Cited

U.S. PATENT DOCUMENTS 1,769,648  7/1930  Raschig ................................. 568/774

Primary Examiner—Werren B. Lone
Attorney, Agent, or Firm—Karl F. Ross

[57] ABSTRACT

4-Chloro-3-methyl-2-isopropyl and 4-chloro-3-methyl-5-isopropyl phenols are effective as bactericides and fungicides, especially against staphylococcus, pneumococcus and tricoccus microorganisms in doses as low as 5 parts per million.

3 Claims, No Drawings

BACTERICIDIC AND FUNGICIDIC CHLOROMETHYLISOPROPYPHENOLS

This application is a division of Ser. No. 357,812 filed 7 May 1973, now U.S. Pat. No. 4,098,828 issued 4 July 1978.

FIELD OF THE INVENTION

Our invention relates to bacteriacidal and fungicidal chloromethylisopropylphenois, to a method of making same and to treatment using these compounds.

OBJECT OF THE INVENTION

The principal object of our invention is to provide efficient and economical agents for the treatment of infectious diseases.

Another object of our invention is to provide stable, odorless and nontoxic agents against staphylococcus, pneumococcus, trichomonas and various fungus diseases.

DESCRIPTION OF THE INVENTION

We have found that the following chloromethylisopropylphenols have valuable properties as therapeutic agents, especially for combatting staphylococcus, pneumococcus, trichomonas and various fungus diseases:

4-chloro-3-methyl-2-isopropyl-phenol (I);
4-chloro-3-methyl-5-isopropyl-phenol (II);
6,6'-methylene-bis (4-chloro-3-methyl-2-isopropyl)-phenol (III); and
2,2'-methylene-bis(4-chloro-3-methyl-5-isopropyl)-phenol (IV).

These compounds have the following valuable properties:

They are characterized by surprisingly high bactero-cide and fungicide activity in comparison with similar products;

They are very stable and do not decompose easily; and

They can be obtained in very pure condition, without any toxic byproduct or trace compound present, by simple conventional processes.

They can be characterized as follows:

APPEARANCE AND ODOR

I, II and III: white crystals having a light odor;
IV: white grains, substantially odor-free.

CHEMICAL NATURE

I and II: 4-chloro-3-methyl-2-isopropyl-phenol and 4-chloro-3-methyl-5-isopropyl-phenol.
Formula Formual $C_{10}H_{13}ClO$
Structural Formula:

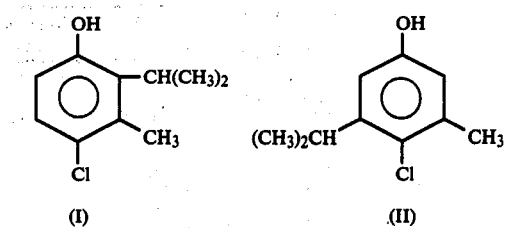

Molecular Weight: 184.66
Elemental Composition in percent (by weight)

| calculated | | C | 65.04 | H | 7.09 | Cl | 19.19 |
|---|---|---|---|---|---|---|---|
| found | (I) | | 65.27 | | 6.93 | | 18.90 |
| | (II) | | 65.10 | | 7.15 | | 19.45 |

III and IV: 6,6'methylene-bis(4-chloro-3-methyl-2-isopropyl; and
2,2'methylene-bis(4-chloro-3-methyl-5-isopropyl) phenol.
Empirical Formula: $C_{21}H_{26}Cl_2O_2$
Structural Formula:

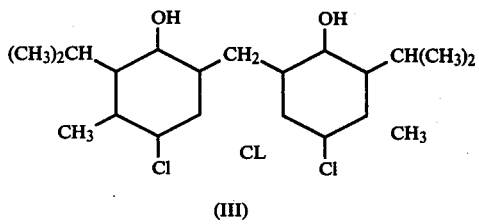

Molecular Weight: 381,34
Elemental Composition in percent (by weight):

| calculated | | C | 66.14 | H | 6.87 | Cl | 18.59 |
|---|---|---|---|---|---|---|---|
| found | (III) | | 66.39 | | 6.82 | | 18.83 |
| | (IV) | | 66.12 | | 6.99 | | 18.51 |

Melting Points: I=52° C.; II=43.5° C., III=130° C.; and IV=175° C.

NUCLEAR MAGNETIC RESONANCE SPECTRUMS

The lines in nuclear magnetic resonance spectrums correspond well with the proposed formulas as far as position (location) and intensity are concerned. Their positions are listed in the following Table:

| Phenol | Solvent | Protons | Type of Multiplet | Multiplet Center |
|---|---|---|---|---|
| I | $CD_3-\underset{\underset{O}{\|\|}}{C}-CD_3$ | CH—(CH$_3$)$_2$ | doublet | 1.36 |
| | | CH$_3$ | singulet | 2.35 |
| | | CH—(CH$_3$)$_2$ | septuplet | 3.38 |
| | | H aromatic | quadruplet | 6.84 |
| | | OH | signal present | |
| II | $CD_3-\underset{\underset{O}{\|\|}}{C}-CD_3$ | CH—(CH$_3$)$_2$ | doublet | 1.17 |
| | | CH$_3$ | singulet | 2.25 |
| | | CH—(CH$_3$)$_2$ | septuplet | 3.31 |
| | | H aromatic | singulet | 6.72 |
| | | OH | signal present | |
| III | CCl$_4$ | CH—(CH$_3$)$_2$ | doublet | 1.32 |
| | | CH$_3$ | singulet | 2.31 |
| | | CH—(CH$_3$)$_2$ | septuplet | 3.35 |
| | | CH$_2$ | singulet | 3.70 |

-continued

| Phenol | Solvent | Protons | Type of Multiplet | Multiplet Center |
|---|---|---|---|---|
| | | OH | singulet | 5.6 |
| | | H aromatic | singulet | 7 |
| IV | CDCL$_3$ | CH—(CH$_3$)$_2$ | doublet | 1.14 |
| | | CH$_3$ | singulet | 2.40 |
| | | CH—(CH$_3$)$_2$ | septuplet | 3.38 |
| | | CH$_2$ | singulet | 4.05 |
| | | H aromatic | singulet | 6.63 |
| | | OH | singulet | 6.63 |

EXAMPLE I 4-chloro-3-methyl-2-isopropyl-phenol and
4-chloro-3-methyl-5-isopropyl-phenol 135 g sulfurylchloride is added slowly to 150 g phenolic base and a reaction takes place at 60°–90° C. When the addition is terminated, the reaction mixture is neutralized with normal caustic potash. The resulting phenolic phase is decanted and washed with distilled water.

The chlorination in this manner of 3-methyl-2-isopropyl-phenol gives 170 g raw product containing approximately 50% by weight of compound I. This raw product can be recovered by distillation and recrystallized in petroleum ether to yield 60 g of pure compound I with a melting point of 52° C. The yield is 32%.

The chlorination of 3-methyl-5-isopropyl-phenol gives 175 g raw product containing approximately 75% by weight of compound II. This raw product is distilled and recrystallized in petroleum ether. The yield is 80 g of II, which is pure and melts at 43.5°C. The yield is 43%.

EXAMPLE 6.6'-methylene-bis(4-chloro-4-methyl-2-isopropyl)-phenol and
2.2'-methylene-bis(4-chloro-3-methyl-2-isopropyl)-phenol.

6.6 g caustic potash is added to 184.6 g of compound I, then 314 g isopropyl alcohol; this mixture is heated to 45° C. and 42 g of 36%-formaldehyde are added. This mixture is maintained at 45° C. and agitated for six hours and then cooled to ambient temperature. The potash is neutralized with 20 g diluted hydrochloric acid and 550 g of petroleum ether are added.

The resulting water phase is decanted and the solvent is completely evaporated. The residue is a brown sticky mass, 190 g, which is redissolved in petroleum ether. Recrystallization gives 75 g of pure compound III, which is a satisfactory yield of 38%.

Compound IV can be prepared in the same manner. The yield is 30%.

The compounds I–IV have excellent therapeutic properties. They can be used for treating infections caused by staphylococcus, pneumococcus and trichomonas and mycosis, e.g. candidosis. They are administered as water solutions by local or topical application, having very low concentrations of the compounds (approximately 5 ppm) and are then most effective and, in addition, are totally nontoxic.

The compounds can be generally described by the formula:

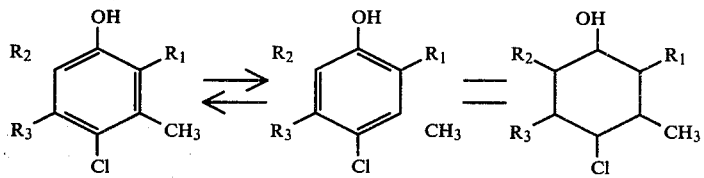

where the members $R_1$, $R_2$ and $R_3$ are each hydrogen, isopropyl or methylenechloromethylisopropylphenol and at least one of the members $R_1$, $R_2$ or $R_3$ is isopropyl.

We claim:
1. A chloromethylisopropylphenol selected from the group which consists of 4-chloro-3-methyl-2-isopropyl-phenol and 4-chloro-3-methyl-5-isopropyl-phenol.
2. The chloromethylisopropylphenol defined in claim 1 which consists of 4-chloro-3-methyl-2-isopropyl-phenol.
3. The chloromethylisopropylphenol defined in claim 1 which consists of 4-chloro-3-methyl-5-isopropyl-phenol.

* * * * *